(12) United States Patent
Kim (10) Patent No.: US 12,102,441 B2
(45) Date of Patent: Oct. 1, 2024

(54) SYSTEM AND METHOD FOR DIAGNOSING SMALL BOWEL CLEANLINESS

(71) Applicant: INTROMEDIC CO., LTD., Seoul (KR)

(72) Inventor: You Jin Kim, Muan-gun (KR)

(73) Assignee: INTROMEDIC CO., LTD., Seoul (KR)

( * ) Notice: Subject to any disclaimer, the term of this patent is extended or adjusted under 35 U.S.C. 154(b) by 263 days.

(21) Appl. No.: 17/612,486

(22) PCT Filed: Oct. 7, 2020

(86) PCT No.: PCT/KR2020/013636
§ 371 (c)(1),
(2) Date: Nov. 18, 2021

(87) PCT Pub. No.: WO2021/091092
PCT Pub. Date: May 14, 2021

(65) Prior Publication Data
US 2022/0304617 A1    Sep. 29, 2022

(30) Foreign Application Priority Data
Nov. 8, 2019  (KR) .................. 10-2019-0142203

(51) Int. Cl.
*A61B 5/00* (2006.01)
*A61B 1/00* (2006.01)
(Continued)

(52) U.S. Cl.
CPC ........ *A61B 5/4255* (2013.01); *A61B 1/00009* (2013.01); *A61B 5/7264* (2013.01);
(Continued)

(58) Field of Classification Search
CPC ... G06T 7/0012; G06T 7/0014; G06T 7/0016; G06T 2207/30028; G06T 2207/10016;
(Continued)

(56) References Cited

U.S. PATENT DOCUMENTS 8,185,185 B2      5/2012  Gilreath et al.
2010/0165088 A1*  7/2010  Seo ...................... A61B 1/0005
                                                348/E7.085
(Continued)

FOREIGN PATENT DOCUMENTS

KR    20160063128 A    6/2016
KR      101889722 B1   8/2018
KR      101928302 B1  12/2018

OTHER PUBLICATIONS

Youxing et al., "A CNN-based Cleanliness Evaluation for Bowel Preparation in Colonoscopy", during the 2019 12th International Congress on Image and Signal processing conference, Oct. 19-21, 2019 (Year: 2019).*

(Continued)

*Primary Examiner* — Boniface N Nganga (57) ABSTRACT

The present invention relates to a system for diagnosing small bowel cleanliness. The system may comprise: a similarity analysis unit for analyzing to select a representative image of similar small bowel images from among a plurality of small bowel images; an image classification unit for, when a series of a plurality of small bowel images in which cleanliness is to be diagnosed are received in a state where the plurality of small bowel images have been learned, classifying small bowel cleanliness according to scores by predicting the small bowel cleanliness by applying the representative image to a learning result; and a cleanliness diagnosis unit for calculating final small bowel cleanliness for the series of the plurality of small bowel images on the (Continued)

basis of a score for small bowel cleanliness of the representative image and the number of small bowel images similar to the representative image.

7 Claims, 8 Drawing Sheets

(51) Int. Cl.
| | |
|---|---|
| *G06F 18/22* | (2023.01) |
| *G06F 18/2413* | (2023.01) |
| *G06N 3/045* | (2023.01) |
| *G06N 3/08* | (2023.01) |
| *G16H 30/20* | (2018.01) |
| *G16H 30/40* | (2018.01) |
| *G16H 50/20* | (2018.01) |
| *G16H 50/50* | (2018.01) |

(52) U.S. Cl.
CPC ............ *A61B 5/7275* (2013.01); *A61B 5/742* (2013.01); *G06F 18/22* (2023.01); *G06F 18/2413* (2023.01); *G06N 3/045* (2023.01); *G16H 30/40* (2018.01); *G16H 50/20* (2018.01); *G06T 2207/30028* (2013.01)

(58) Field of Classification Search
CPC ........... G06T 2207/10024; G06T 2207/10068; G06N 3/0464; A61B 1/041; A61B 1/0009
USPC ......................................................... 382/128
See application file for complete search history.

(56) References Cited

U.S. PATENT DOCUMENTS

2016/0148376 A1* 5/2016 Ryu .................... A61B 8/00
382/131
2020/0397238 A1* 12/2020 Dray .................... G06N 20/20

OTHER PUBLICATIONS

Pogorelov et al., "KVASIR: a Multi-Class Image Dataset for Computer Aided Gastrointestinal Disease Detection", Proceedings of the 8th ACM on multimedia systems conference, pp. 164-169, Jun. 20, 2017.

* cited by examiner

SYSTEM AND METHOD FOR DIAGNOSING SMALL BOWEL CLEANLINESS

TECHNICAL FIELD

The disclosure relates to a system and method for diagnosing small-bowel cleanliness, and more particularly to a system and method for displaying cleanliness of a small bowel on a user interface (UI) by previous learning and automatic diagnosis.

BACKGROUND ART

A small bowel refers to a digestive tract that lies between the stomach and the large bowel and is 6~7 m long, and is an important organ to digest and absorb nutrients in digestion. The small bowel is divided into three regions, i.e., duodenum, jejunum and ileum from above.

Cleanliness of the small bowel is information required to be filled in when a diagnostic report is made after diagnosing conditions of the small bowel. At present, a medical specialist learns more than tens of thousands of images about the small bowel, and the cleanliness is diagnosed by the specialist's decision based on the learned images.

However, such a conventional diagnosis about the cleanliness of the small bowel has a problem of inconsistency because the specialist makes a subjective decision by diagnosing the cleanliness of the small bowel for himself/herself and thus different specialists who diagnose the cleanliness of the small bowel are highly likely to make different decisions. Accordingly, there is a need for a system that automatically diagnose and objectify the cleanliness of the small bowel.

DISCLOSURE

Technical Problem

The disclosure is conceived to solve the foregoing conventional problems, and an aspect of the disclosure is to objectively and consistently diagnose cleanliness of a small bowel.

Technical Solution

To achieve the aspect of the disclosure, there is provided a system for diagnosing small-bowel cleanliness, including: a similarity analysis unit configured to perform analysis for selecting a representative image of similar small-bowel images from among a plurality of small-bowel images; an image classification unit configured to classify a plurality of small-bowel images according to scores for small-bowel cleanliness by predicting the small-bowel cleanliness by applying the representative image to a learning result when a series of a plurality of small-bowel images of which the cleanliness is desired to be diagnosed is received in a state that a plurality of small-bowel images has been learned, and; and a cleanliness diagnosis unit configured to calculate final small-bowel cleanliness about the series of the plurality of small-bowel images based on points of the representative image scored for the small-bowel cleanliness and the number of small-bowel images similar to the representative image.

Here, the similarity analysis unit may be configured to select a representative image by measuring similarity based on comparison in a color histogram between two small-bowel images through a Bhattacharyya distance algorithm and selecting the representative image from among the plurality of small-bowel images selected based on a given similarity reference.

Further, the similarity reference converges into '0' as similarity between two small-bowel images decreases, and converges into '1' as the similarity increases.

Furthermore, the image classification unit may be configured to learn color and texture characteristics of the plurality of small-bowel images based on convolutional neural network (CNN) model, and predict small-bowel cleanliness by applying the small-bowel images to the learning result based on landmark information.

In addition, the image classification unit may be configured to perform learning after standardizing color references of the plurality of small-bowel images output from a plurality of image sensors.

Furthermore, the color references may employ at least one of RGB, hue saturation value (HSV), and color coordinates (Lab).

Further, the plurality of small-bowel images may have been scored on a scale of '1' to '10' for small-bowel cleanliness.

Furthermore, the final small-bowel cleanliness may be obtained by multiplying the number of similar images corresponding to 1 to $n^{th}$ representative images by points of scored cleanliness, summing up the multiplication results, and dividing the sum by a total number of the plurality of small-bowel images.

In addition, the image classification unit may be configured to learn a small-bowel region based on color and texture in the plurality of small-bowel images, and classifies the plurality of small-bowel images according to the small-bowel regions based on landmark information set in the small-bowel region.

To achieve the aspect of the disclosure, there is provided a method of diagnosing small-bowel cleanliness, including: receiving a plurality of small-bowel images that have been scored; learning the plurality of small-bowel images that have been scored; performing analysis for selecting a representative image of similar small-bowel images from among the plurality of small-bowel images when a series of a plurality of small-bowel images of which small-bowel cleanliness is desired to be diagnosed is received; classifying a plurality of small-bowel images according to scores for the small-bowel cleanliness by predicting small-bowel cleanliness by applying the representative image to a learning result; and calculating final small-bowel cleanliness about the plurality of small-bowel images based on the representative image.

Advantageous Effects

According to the disclosure, a system and method for diagnosing small-bowel cleanliness have effects as follows.

First, it is possible to provide a consistent and objective index for small-bowel cleanliness. In the system and method for diagnosing the small-bowel cleanliness according to the disclosure, the system previously learns a lot of pictures or images about a small bowel and automatically diagnoses the small-bowel cleanliness, thereby more consistently providing the small-bowel cleanliness unlike conventional small-bowel cleanliness inconsistently diagnosed based on a specialist's subjective decision.

Second, it is possible to save time. In the system and method for diagnosing the small-bowel cleanliness according to the disclosure, the small-bowel cleanliness is instantly diagnosed based on a learned algorithm when a picture of a small bowel desired by a user to be diagnosed based on a picture or image of a previously learned small bowel is input, thereby diagnosing the small-bowel cleanliness in a short time, and thus saving time to be taken in diagnosing the small-bowel cleanliness.

Third, it is possible to offer convenience. As mentioned above, it is easy for a user to diagnose the small-bowel cleanliness because the small-bowel cleanliness is instantly diagnosed based on the learned algorithm when a picture of a small bowel desired by a user to be diagnosed is input.

MODE FOR CARRYING OUT DISCLOSURE

Below, embodiments of the disclosure will be described in detail with reference to the accompanying drawings. However, some features unrelated to the gist of the disclosure may be omitted or summarized, but the omitted features are not unnecessary for the disclosure and may be used as combined by a person having ordinary skills in the art to which the disclosure pertains.

<A System for Diagnosing Small-Bowel Cleanliness>

Figure 1:
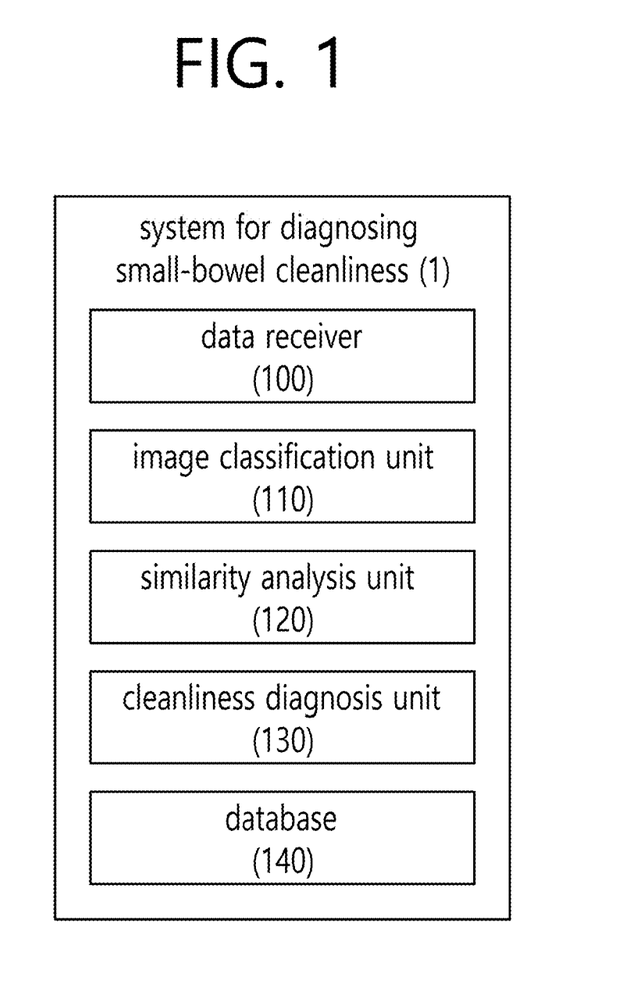
FIG. 1 is a block diagram of a system for diagnosing small-bowel cleanliness of according to an embodiment of the disclosure.

FIG. 1 is a block diagram of a system for diagnosing small-bowel cleanliness of according to an embodiment of the disclosure.

As shown in FIG. 1, the system for diagnosing the small-bowel cleanliness according to an embodiment of the disclosure may include a data receiver 100, an image classification unit 110, a similarity analysis unit 120, a cleanliness diagnosis unit 130, and a database 140.

The data receiver 100 is configured to receive a plurality of small-bowel images from a specialist. The data receiver 100 may be connected to a terminal of the specialist through a wired/wireless network to receive information. The specialist may rate the plurality of small-bowel images with scores of '1' to '10' for the small-bowel cleanliness according to easiness of review and diagnosis. Here, the plurality of small-bowel images may include tens of thousands of small-bowel images.

The image classification unit 110 is configured to score and classify representative images in the small-bowel cleanliness when a series of a plurality of small-bowel images is received in real time after learning the cleanliness of the small bowel based on the plurality of small-bowel images received in the data receiver 100. The image classification unit 110 may learn a plurality of small-bowel images based on an artificial neural network. In this case, the plurality of small-bowel images may be learned based on a convolutional neural network (CNN) model. The small-bowel image is scored on a scale of '1' to '10' for the small-bowel cleanliness, and the image classification unit 110 learns color and texture characteristics of the small-bowel image based on the scores in connection with the small-bowel image scored on the scale of '1' to '10' for the small-bowel cleanliness and predicts the small-bowel cleanliness by applying an image of a small bowel region to a learning result based on landmark information, thereby classifying the small-bowel images according to the scores for the small-bowel cleanliness when a series of plurality of small-bowel images is input later.

The similarity analysis unit 120 is configured to perform analysis to select a representative image of similar small-bowel images from among the series of the plurality of small-bowel images received from the data receiver 100 in real time. The similarity analysis unit 120 selects the representative image by analyzing whether two small-bowel images among the plurality of small-bowel images are the similar small-bowel images, so that the image classification unit 110 can classify the plurality of small-bowel images with respect to the small-bowel, and thus the cleanliness diagnosis unit 130 can quickly diagnose final small-bowel cleanliness. The similarity analysis unit 120 employs a similarity algorithm to select only the representative image of the similar small-bowel images, thereby allowing the image classification unit 110 to classify the plurality of small-bowel images with respect to the small-bowel cleanliness without analyzing all the tens of thousands of small-bowel images. In this way, the similarity analysis unit 120 speeds up the classification of the small-bowel images when the small-bowel cleanliness is diagnosed, thereby helping to optimize the system 1 for diagnosing the small-bowel cleanliness.

The cleanliness diagnosis unit 130 is configured to calculate the final small-bowel cleanliness of the small-bowel images in the state that the series of the plurality of small-bowel images is received in real time. The final small-bowel cleanliness is required to be calculated by considering how many similar images the representative image represents. In other words, the small-bowel images are different in the small-bowel cleanliness according to the regions of the small bowel. Therefore, the small-bowel cleanliness is finally diagnosed based on average of small-bowel cleanliness with regard to the series of the plurality of received small-bowel images by summing up the scores according to the regions of the small bowel.

The database 140 is configured to make the plurality of small-bowel images received from the specialist be stored and preserved according to the scores for the small-bowel cleanliness. Further, the database 140 may also store and preserve a history of the small-bowel cleanliness that has been diagnosed by the cleanliness diagnosis unit 130.

Below, a method of diagnosing the small-bowel cleanliness according to the disclosure will be described.

Figure 2:
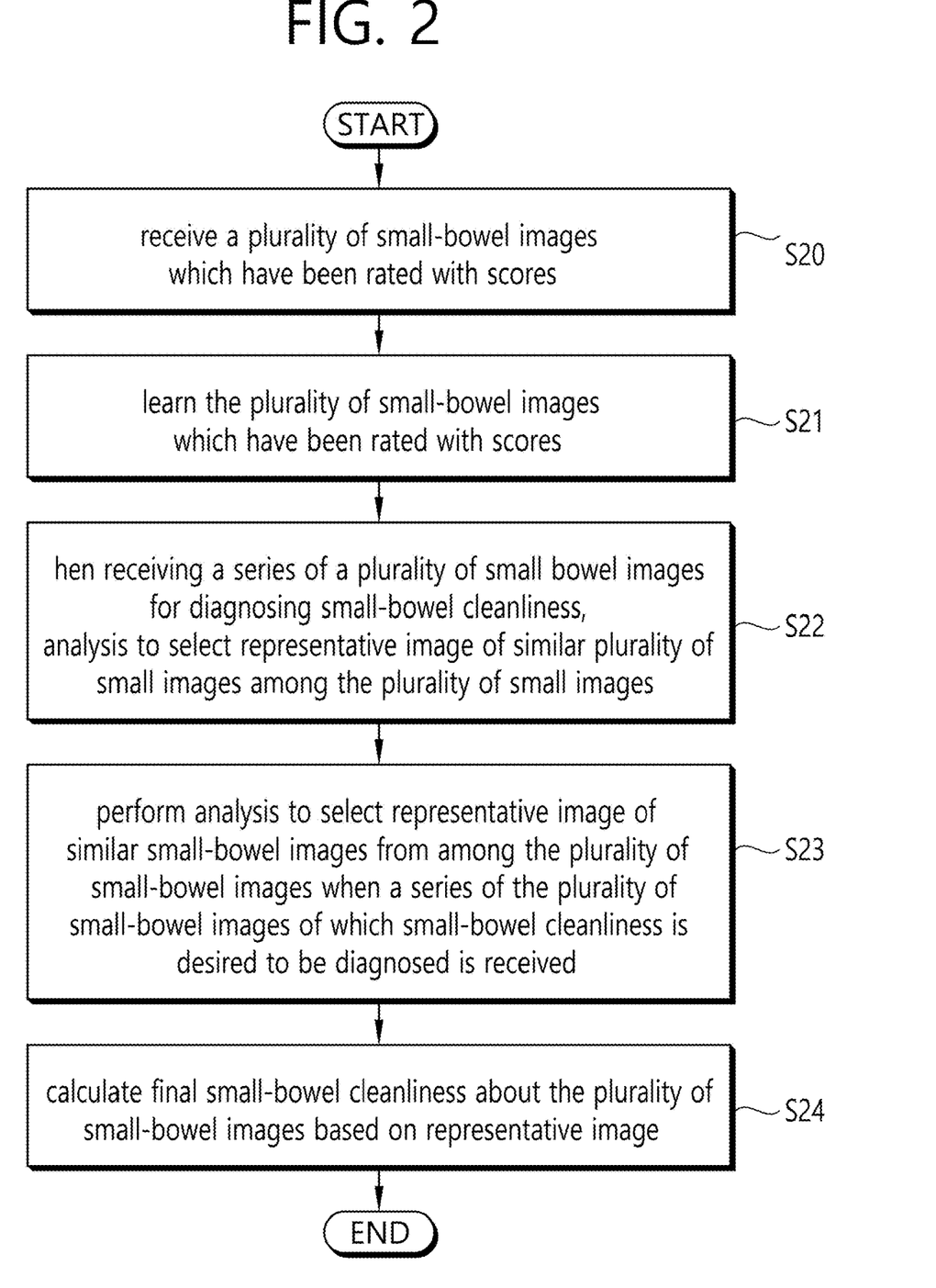
FIG. 2 is a flowchart showing a method of diagnosing small-bowel cleanliness according to an embodiment of the disclosure.

FIG. 2 is a flowchart showing a method of diagnosing small-bowel cleanliness according to an embodiment of the disclosure.

As shown in FIG. 2, by the method of diagnosing the small-bowel cleanliness according to an embodiment of the disclosure, a plurality of small-bowel images which have already been rated with scores are received at first. <S20>

Here, the plurality of small-bowel images, of which the scoring has been completed, will be further described in detail. To this end, the description will be made with reference to FIG. 3.

Figure 3:
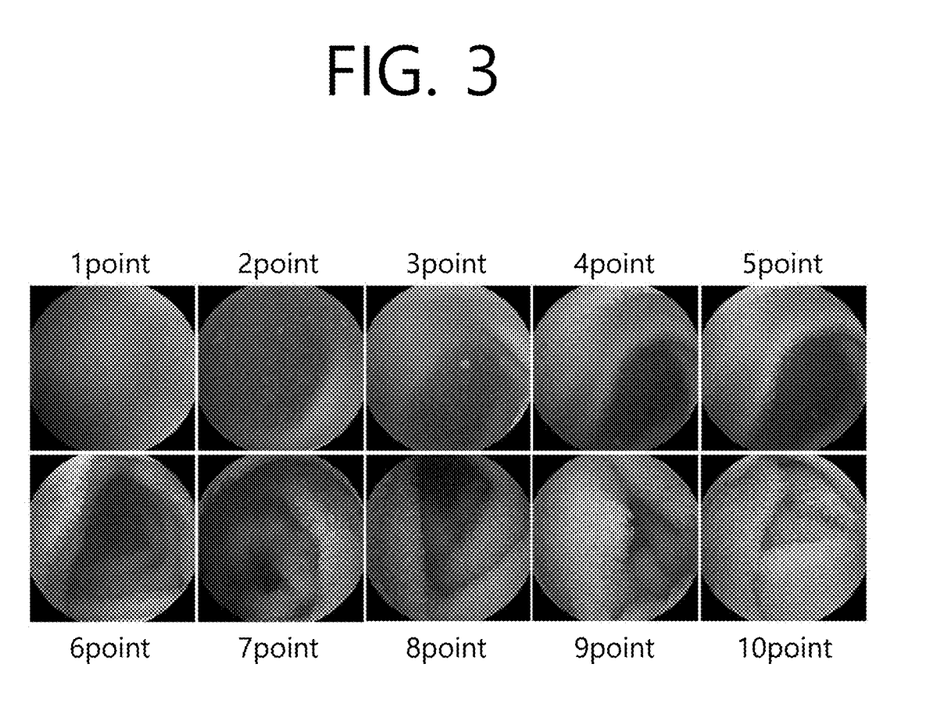
FIG. 3 illustrates that small-bowel images have been rated with scores for small-bowel cleanliness in the system for diagnosing the small-bowel cleanliness according to an embodiment of the disclosure.

FIG. 3 illustrates that small-bowel images have been rated with scores for small-bowel cleanliness in the system for diagnosing the small-bowel cleanliness according to an embodiment of the disclosure.

As shown in FIG. 3, the small-bowel images may be scored on the scale of '1' to '10' for the small-bowel cleanliness. Specifically, the scores for the small-bowel cleanliness may be rated by the specialist's subjective decision made while looking at the small-bowel images based on various experiences. In this case, the specialist rates the small-bowel cleanliness based on image definition of a small bowel on the small-bowel image, a proportion of a part corresponding to the small bowel in the whole image, and floating matters on the image.

Referring to FIG. 3, when the small-bowel cleanliness is scored '1' point, the shape of the small bowel is hardly seen on the small-bowel image and not definite. Therefore, the specialist may determine the small-bowel cleanliness of the corresponding small-bowel image as the '1' point.

Further, when the small-bowel cleanliness is scored '2' points, that the outline, the inner wall, and the like shapes of the small bowel are more definite than those of the '1' point, but there are a lot of floating matters. Therefore, the specialist may determine the small-bowel cleanliness of the corresponding small-bowel image as the '2' points.

In addition, when the small-bowel cleanliness is scored '10' points, that the small bowel is very definitely seen on the small-bowel image, not only the inner wall of the small bowel but also villi are observable, and there are few floating matters. Therefore, the specialist may determine the small-bowel cleanliness of the corresponding small-bowel image as the '10' points.

Information about the small-bowel images scored as above by the specialist with regard to a plurality of small-bowel images may be received in the data receiver 100 and then stored in the database 140 according to the scores for the small-bowel cleanliness.

Next, the image classification unit 110 learns the plurality of small-bowel images, the scoring of which has been completed. <S21>

The image classification unit 110 may use the artificial neural network to learn the small-bowel images rated by the specialist with the scores for the small-bowel cleanliness. This process will be described in detail with reference to FIGS. 4 and 5.

Figure 4:
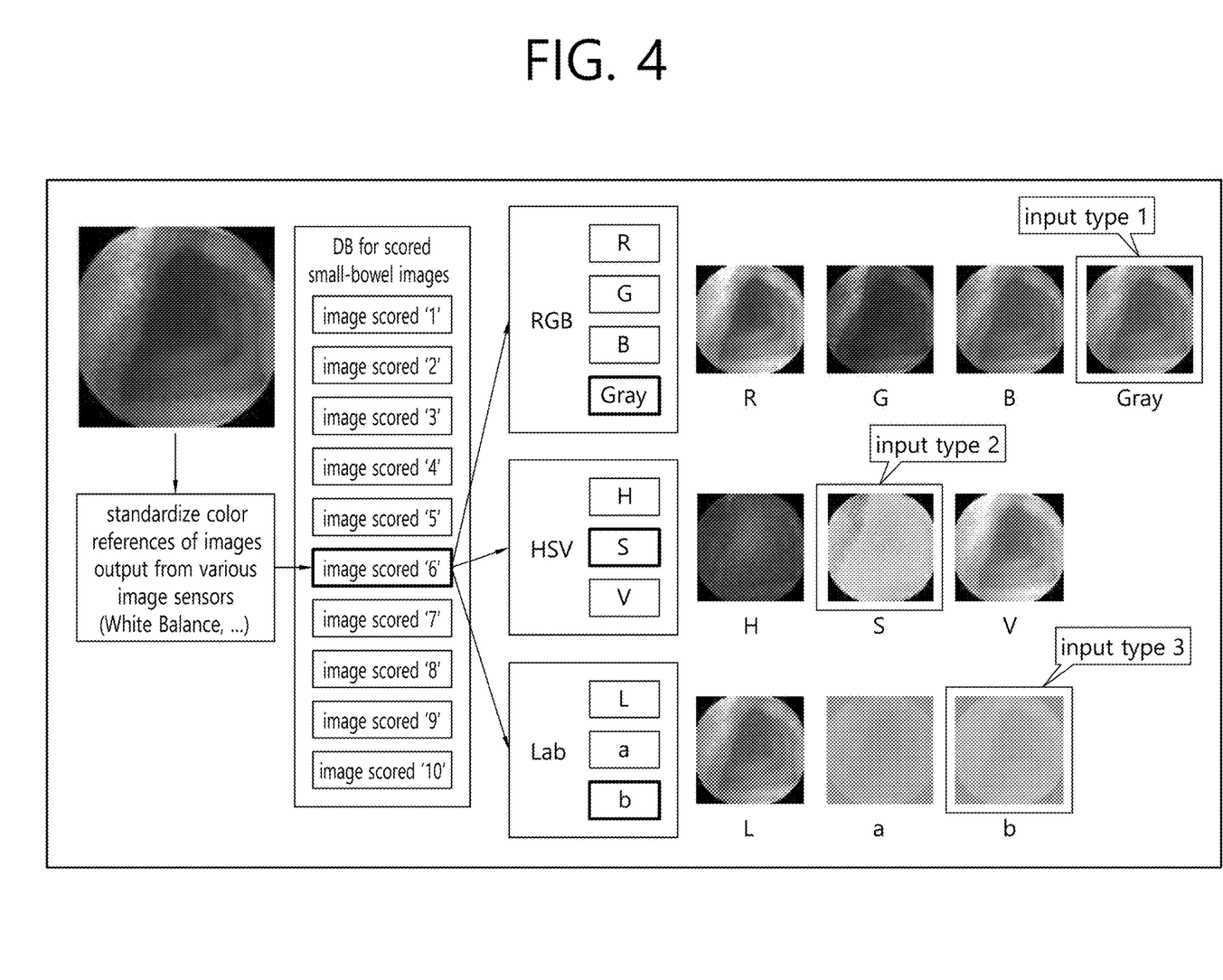
FIG. 4 schematically illustrates that a plurality of color references are standardized before learning the small-bowel images based on a convolutional neural network (CNN) model in the system for diagnosing the small-bowel cleanliness according to an embodiment of the disclosure.
Figure 5:
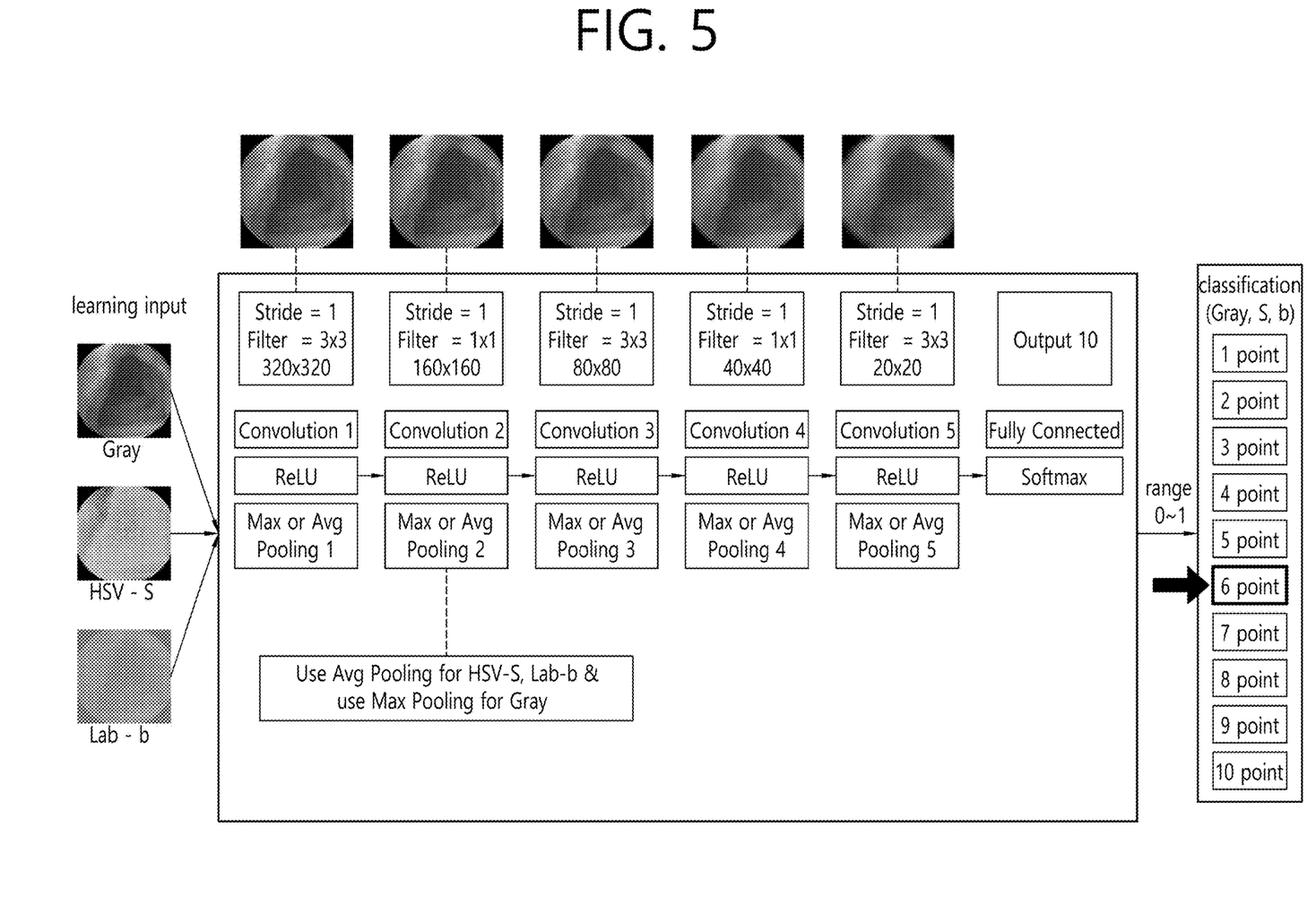
FIG. 5 schematically illustrates that the small-bowel images are learned based on the CNN model in the system for diagnosing the small-bowel cleanliness according to an embodiment of the disclosure.

FIG. 4 schematically illustrates that a plurality of color references are standardized before learning the small-bowel images based on a CNN model in the system for diagnosing the small-bowel cleanliness according to an embodiment of the disclosure, and FIG. 5 schematically illustrates that the small-bowel images are learned based on the CNN model in the system for diagnosing the small-bowel cleanliness according to an embodiment of the disclosure.

First, as shown in FIG. 4, the image classification unit 110 may apply pre-processing to the small-bowel images before learning the plurality of small-bowel images. Specifically, the plurality of small-bowel images are received from various image sensors and thus different in color reference. In other words, the small-bowel images may be different in red, blue, green (RGB), hue saturation value (HSV), and color coordinates (Lab) even though the small-bowel images are rated with the same score for the small-bowel cleanliness, and therefore it is required to standardize the color references to definitely learn the plurality of small-bowel images. the color reference is used as a learning input.

For example, as shown in FIG. 4, when small-bowel images scored '6 points' for the small-bowel cleanliness are learned, the small-bowel images scored '6 points' for the small-bowel cleanliness may be different in color references because the images are received from various image sensors. Thus, the image classification unit 110 may apply the pre-processing to the plurality of small-bowel images in such a manner that gray scale converted from RGB, S selected from HSV and b selected from Lab of the images scored '6' points for the small-bowel cleanliness are input.

Thus, the image classification unit 110 can perform the learning based on the color references standardized by making the plurality of small-bowel images, which are stored according to the scores for the small-bowel cleanliness, undergo the pre-processing according to the scores for the small-bowel cleanliness. Further, the image classification unit 110 may apply the pre-processing to the plurality of small-bowel images based on the standardized color references with regard to all the scores from '1' to '10' points for the small-bowel cleanliness.

In addition, as shown in FIG. 5, the image classification unit 110 according to the disclosure may use the artificial neural network to learn the plurality of small-bowel images. Specifically, the image classification unit 110 may perform the learning based on matching between the state of the small-bowel image and the score for the small-bowel cleanliness with regard to the plurality of small-bowel images stored according to the scores for the small-bowel cleanliness. In this case, the artificial neural network may use a CNN model in learning the plurality of small-bowel images.

In general, the CNN refers to an artificial neural network that consists of an input layer and an output layer as well as multiple hidden layers and employs a mathematical operation of convolution. The hidden layers of the CNN generally include a series of convolutional layers related to multiplication or other inner products. An activation function is commonly a rectified linear unit (ReLU) layer, and is followed by additional convolution such as pooling layers, fully connected layers and normalization layers, which are called hidden, because inputs and outputs are masked by the activation function and final convolution. Such CNN has a structure suitable for learning two-dimensional data, and may be trained through a backpropagation algorithm. The CNN model is one of representative models widely used in various application fields such as object classification, object detection, etc. in images, and thus used for classifying the images. According to the disclosure, the image classification unit 110 may perform the learning based on the CNN model and classify the plurality of small-bowel images. The CNN is publicly known and therefore its detailed descriptions will be omitted.

For example, it will be assumed as shown in FIG. 5 that five small-bowel images are learned. The five images include a first small-bowel image having Stride=1, Filter=3×3, and width and height of 320×320; a second small-bowel image having Stride=1, Filter=1×1, and width and height of 160×160; a third small-bowel image having Stride=1, Filter=3×3, and width and height of 80×80; a fourth small-bowel image having Stride=1, Filter=1×1, and width and height of 40×40; and a fifth small-bowel image having Stride=1, Filter=3×3, and width and height of 20×20.

Thus, the image classification unit 110 uses the CNN to apply convolution1 to the first small-bowel image to thereby undergo Pooling or Avg Pooling via the ReLU layer. Like the first small-bowel image, the second small-bowel image, the third small-bowel image, the fourth small-bowel image and the fifth small-bowel image are respectively subjected to convolution2, convolution3, convolution4 and convolution5 to thereby undergo the ReLU layer and the Max Pooling or Avg Pooling.

Here, when the RGB, HSV and Lab are set as the learning inputs, the Avg Pooling is used at the S scale of the HSV and the b scale of the Lab, and the Max Pooling is used at the gray of the RGB.

In this case, the color and texture characteristics of the small-bowel image are learned when the small-bowel cleanliness is learned. In other words, the small-bowel images are different in characteristics such as definition, color and texture according to the scores. Therefore, the image classification unit 110 performs the learning by sorting out the color and texture of the small-bowel image scored '1', the color and texture of the small-bowel image scored '2', and the color and texture of the small-bowel image scored '10', thereby learning the characteristics about the scores for the small-bowel cleanliness.

Further, to distinguish between the regions of the small bowel, small-bowl regions may be learned based on landmark information. In other words, a landmark is set based on the characteristics of the villi or inner wall of the small bowel, and used to distinguish between the regions of the small bowel. Through the distinguishment between the small-bowel regions, the image classification unit 110 may sort out the scores for the small-bowel cleanliness according to the regions of the small bowel. For such landmark information, a specific mark set by a system user may be used.

With such a process, the image classification unit 110 may learn an image scored '6' points for the small-bowel cleanliness when the Gray, S and b are used as the color references.

When a series of a plurality of small-bowel images of which the small-bowel cleanliness is desired to be diagnosed is received, analysis is performed to select a representative image of similar small-bowel images from among the plurality of small-bowel images. <S22>

Similarity analysis among the plurality of small-bowel images the similarity will be described with reference to FIG. 6.

Figure 6:
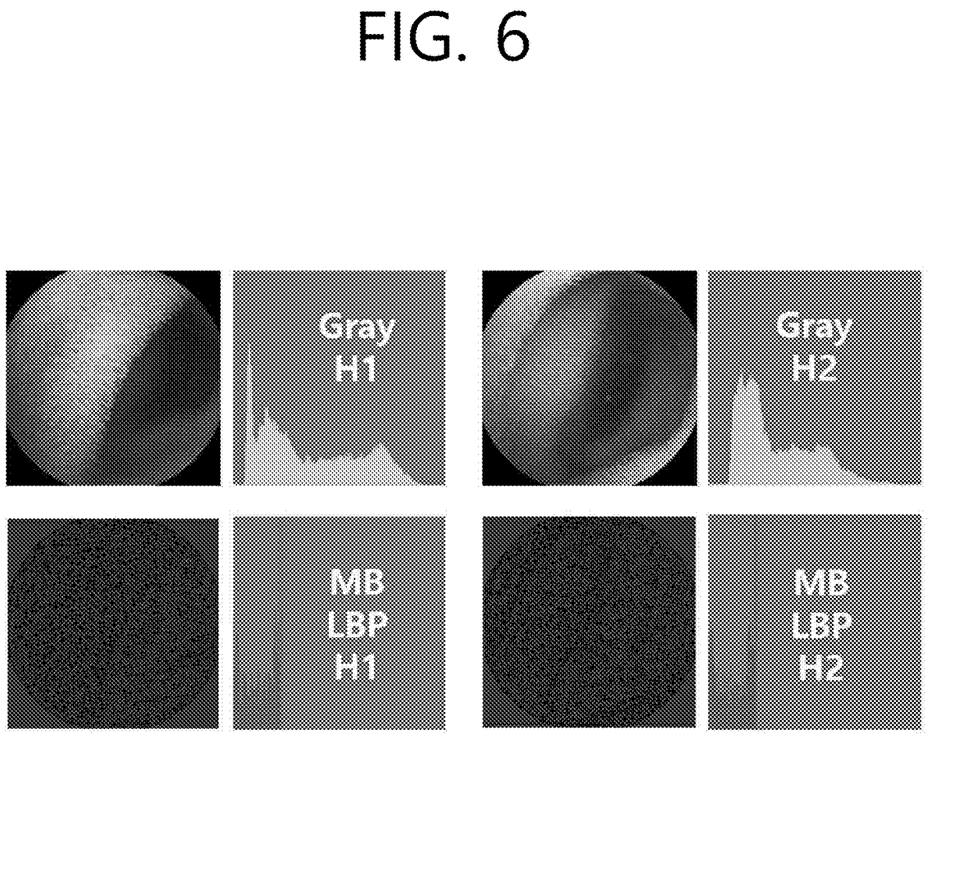
FIG. 6 schematically illustrates that two small-bowel images are compared in a color histogram by a Bhattacharyya distance algorithm used in the system for diagnosing the small-bowel cleanliness according to an embodiment of the disclosure.

FIG. 6 schematically illustrates that two small-bowel images are compared in a color histogram by a Bhattacharyya distance algorithm used in the system for diagnosing the small-bowel cleanliness according to an embodiment of the disclosure.

As shown in FIG. 6, the similarity analysis unit 120 may select the representative image by analyzing small-bowel images, which are similar in small-bowel cleanliness, among the plurality of small-bowel images. Such selection of the representative image among the plurality of small-bowel images speeds up the process of diagnosing the small-bowel cleanliness, thereby making it possible to diagnose the small-bowel cleanliness in a short time.

According to the disclosure, the similarity analysis unit 120 may use the Bhattacharyya distance algorithm to analyze the similarity between the small-bowel images. The Bhattacharyya distance algorithm has been known as digital image processing technology that measures statistical separability of spectroscopic magnitudes when provability values of correct classification are given. The Bhattacharyya distance algorithm is the strongest algorithm among the algorithms for obtaining a distance between two distributions. In other words, the similarity analysis unit 120 can measure the similarity based on comparison in the color histogram between two small-bowel images. Thus, the similarity based on comparison in the color histogram between two images converges into "0" as the similarity increases, but the similarity converges into "1" as the similarity decreases.

FIG. 6 illustrates such color histograms. The color histogram may use the gray scale as a comparison type, or may use a local binary pattern (LBP) or multi-block local binary pattern (MB-LBP) image mode. Here, the LBP refers to a type of visual descriptor used for classification in computer vision. The LBP is publicly known and therefore its detailed descriptions will be omitted. Therefore, the similarity analysis unit 120 may convert the plurality of small-bowel images into those of the comparison type for comparison in the color histogram.

The color histogram will be described in detail. In FIG. 6, two upper small-bowel images were converted by the similarity analysis unit 120 into the color histograms H1 and H2 based on the gray scale. The color histograms of such two small-bowel images show a pattern that rises at a left side but goes down rightward. Further, two lower small-bowel images in FIG. 6 were converted by the similarity analysis unit 120 into the color histograms H1 and H2 based on the MB-LBP mode. The color histograms of such two small-bowel images may be approximately patterned in the form of 'ㅂ'.

The similarity analysis unit 120 may measure the similarity between two small-bowel images by comparing the color histograms based on the color histogram of the gray scale or the color histogram of the LBP image mode.

Specifically, the similarity analysis unit 120 may calculate a Bhattacharyya distance d(H1, H2) with respect to the color histograms of the two small-bowel images. Here, H1 and H2 refer to the color histograms of the two small-bowel images as described above, $\overline{H1}$ and $\overline{H2}$ are average color histograms of the two small-bowel images, I is a pixel value, and N is a total number of bins in the color histograms.

Therefore, the similarity analysis unit 120 can calculate the Bhattacharyya distance d(H1, H2) based on such elements as follows.

$$d(H1, H2) = \sqrt{1 - \frac{1}{\sqrt{\overline{H1}\,\overline{H2}}\,N^2} \sum_I \sqrt{H1(I) \cdot H2(I)}}$$

The distance between two distributions is calculated based on the calculated Bhattacharyya Distance, and it is thus possible to compare the color histograms of the two small-bowel images and measure the similarity. The similarity is calculated as a value between '0' and '1', and converges into "0" as the similarity decreases but into "1" as the similarity increases when two images are compared in the color histogram.

Figure 7:
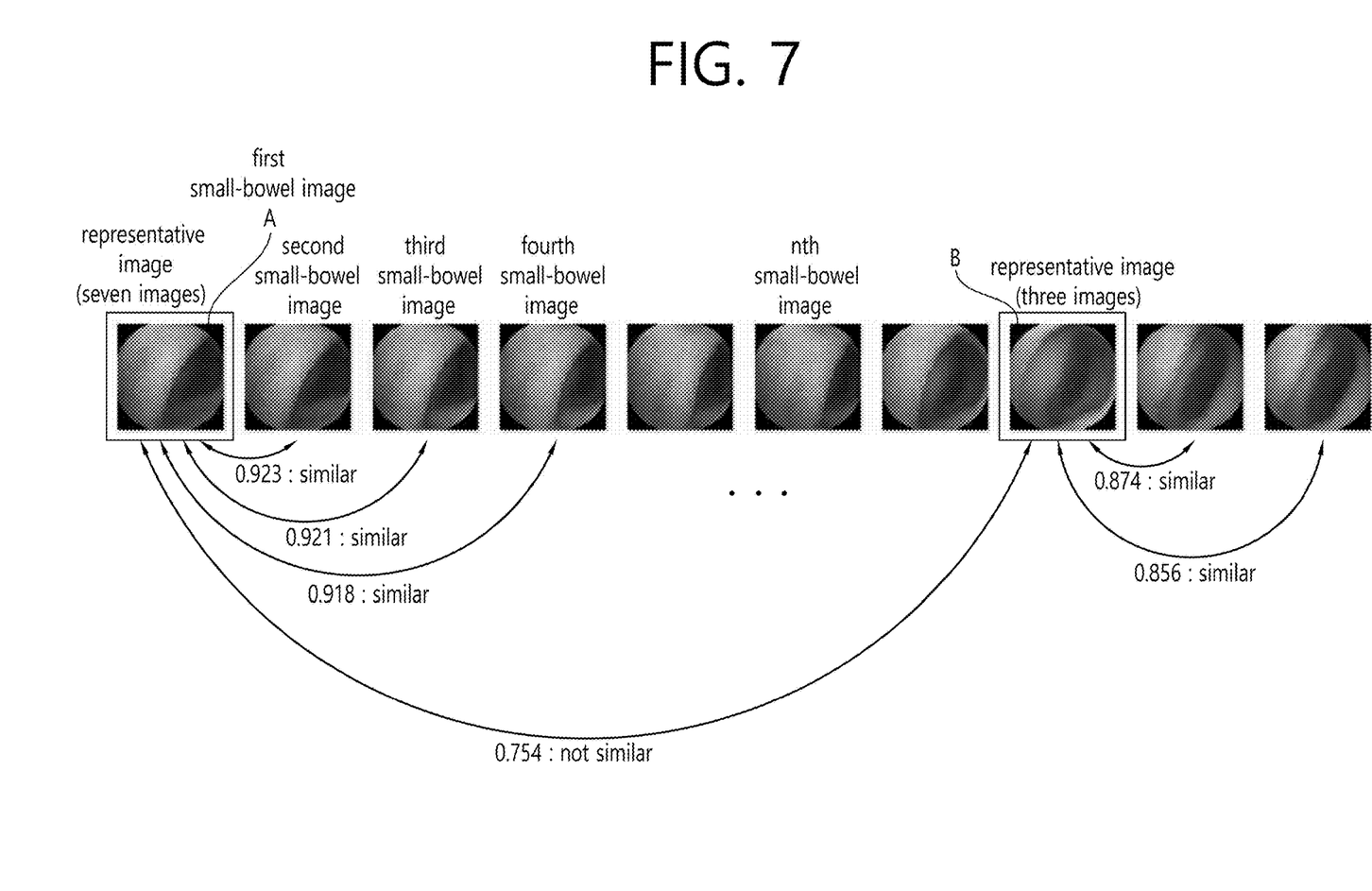
FIG. 7 schematically illustrates that a representative image is selected based on similarity in the system for diagnosing the small-bowel cleanliness according to an embodiment of the disclosure.

Further, it will be described that the representative image is selected from among the small-bowel images between which the similarities are analyzed.

FIG. 7 schematically illustrates that a representative image is selected based on similarity in the system for diagnosing the small-bowel cleanliness according to an embodiment of the disclosure.

As shown in FIG. 7, the similar small-bowel images are selected by comparing the plurality of small-bowel images after the similarity analysis unit 120 measures the similarities.

Specifically, the representative image may be selected by repetitively comparing the similarity between the two small-bowel images with a reference similarity on the successive frames of the small-bowel regions. For example, it will be assumed that the reference similarity is '0.850.' In this case, as shown in FIG. 7, the similarity analysis unit 120 selects one of the small-bowel images compared at the very first as the representative image, and performs analysis based on comparison between this small-bowel image and the subsequent small-bowel images, thereby selecting the representative image and the similar small-bowel images.

In other words, referring to FIG. 7, the leftmost first small-bowel image is compared with the second, third, . . . , $n^{th}$ small-bowel images on the first small-bowel image's right side in sequence. As a result, the second small-bowel image has a similarity of '0.923' with the first small-bowel image, which is higher than the reference similarity of '0.850', and it is thus analyzed that the first small-bowel image and the second small-bowel image are similar. Between them, the similarity analysis unit 120 may select the first small-bowel image as a representative image A and then compare and analyze the subsequent small-bowel images. Likewise, the first small-bowel image and the third small-bowel image are equally subjected to the Bhattacharyya distance algorithm, and then the similarity analysis unit 120 compares and analyzes the histograms of the two small-bowel images. As a result, a similarity of '0.921' is obtained, which is higher than the reference similarity of '0.850', thereby analyzing that the first small-bowel image and the third small-bowel image are similar to each other. In addition, the fourth small-bowel image and the first small-bowel image are compared, and a similarity of '0.918' is obtained, which is higher than the reference similarity of '0.850', thereby analyzing that the first small-bowel image and the fourth small-bowel image are similar to each other.

In this way, the similarity analysis unit 120 may compare and analyze the representative image and other images to thereby calculate the similarity of the $n^{th}$ small-bowel image, and the similar small-bowel images may fall into a small-bowel image group to which the representative image belongs. In this case, if a small-bowel image of which the similarity is lower than the reference the similarity of '0.850' is present, a new representative image is selected.

Specifically, it is analyzed that the representative images A and B of the small-bowel images are not similar because the similarity of '0.754' between the two small-bowel images is lower than the reference the similarity of '0.850'. Therefore, the similarity analysis unit 120 may select similar images by regarding the small-bowel image B as a new representative image. When the small-bowel images following the representative image B are compared with the representative image B like the images similar to the representative image A, the similarities of '0.874' and '0.856' are obtained. Therefore, it is analyzed that the two small-bowel images are similar to the representative image B. Accordingly, a small-bowel image group to which the representative image B belongs may be selected.

Next, the small-bowel cleanliness is predicted by applying the representative image to the learning result, thereby classifying the small-bowel images according to the scores for the small-bowel cleanliness. <S23>

With the plurality of learned small-bowel images, the image classification unit 110 classifies the plurality of small-bowel images, which are received in real time, with respect to the small-bowel cleanliness, based on the representative images previously selected by the similarity analysis unit 120 from among the plurality of small-bowel images. In other words, the scores for the small-bowel cleanliness may be given on the scale of '1' to '10', and the image classification unit 110 may classify the representative images according to the scores from '1' point to '10' points based on the learning results, and may also classify the small-bowel images, which are selected as similar to the representative image, together with the representative images according to the scores.

Last, the final small-bowel cleanliness about the plurality of small-bowel images is calculated based on the representative image. <S24>

It will be described with reference to FIG. 8 that the cleanliness diagnosis unit 130 finally calculates the small-bowel cleanliness.

Figure 8:
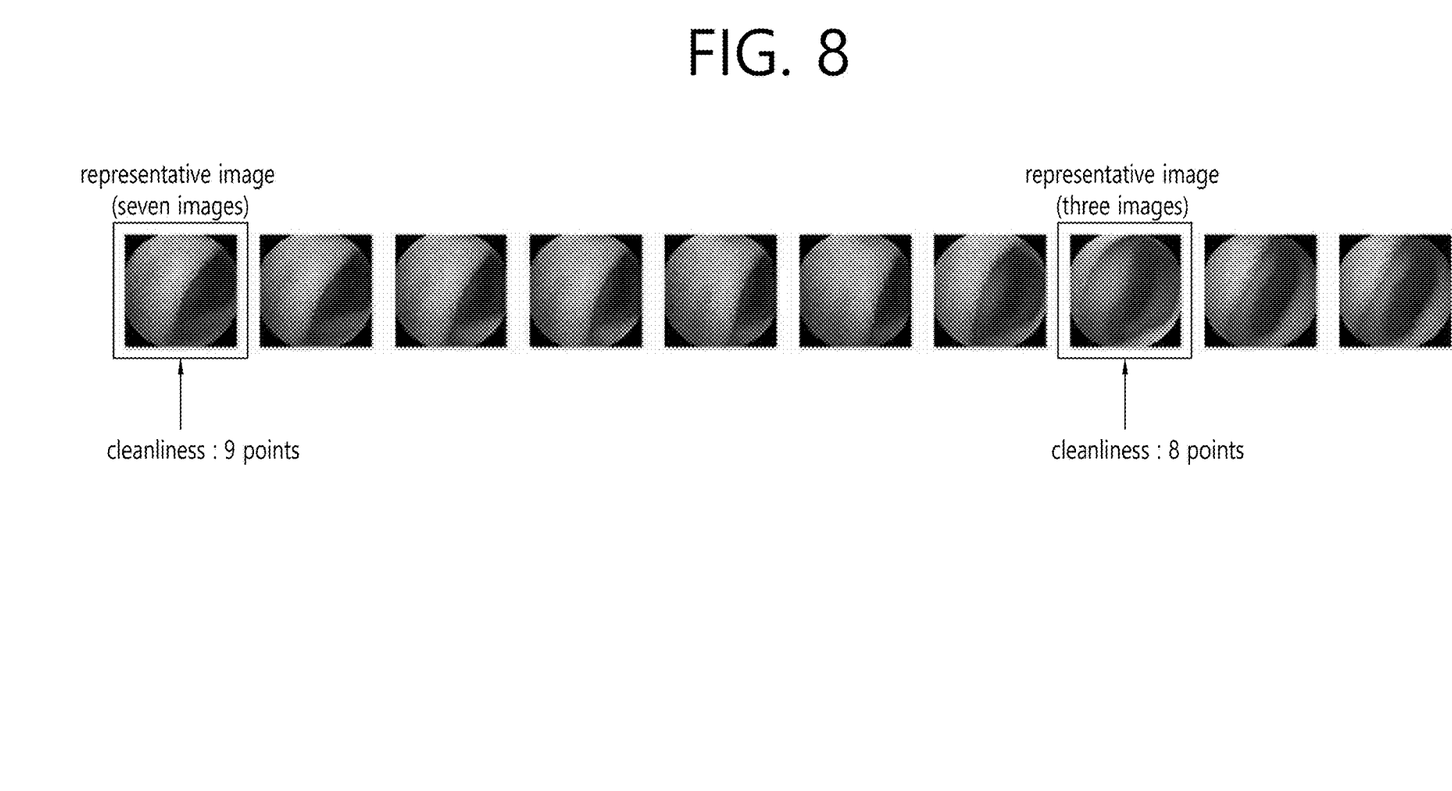
FIG. 8 schematically illustrates that the small-bowel cleanliness is finally calculated in the system for diagnosing the small-bowel cleanliness according to an embodiment of the disclosure.

FIG. 8 schematically illustrates that the small-bowel cleanliness is finally calculated in the system for diagnosing the small-bowel cleanliness according to an embodiment of the disclosure.

As shown in FIG. 8, the final small-bowel cleanliness may be diagnosed considering how many small-bowel images the representative image represents among the similar small-bowel images.

Specifically, the final small-bowel cleanliness is obtained by multiplying the number of similar small-bowel images, which the representative image represents, by the small-bowel cleanliness of the representative image, summing up the multiplication results of all the representative images, and dividing the sum by the total number of small-bowel images. In other words, the final small-bowel cleanliness is diagnosed based on average small-bowel cleanliness of all the small-bowel images. This is expressed as follows.

Final small-bowel cleanliness={(the number of similar images the representative image $A$ represents $x$ the score of '1' point for small-bowel cleanliness)+ . . . +(the number of similar images the representative image $n$ represents $x$ the score of '$n$' points for small-bowel cleanliness)}/the total number of small-bowel images For example, it will be assumed that the plurality of small-bowel images received by the data receiver 100 in real time are scored for the small-bowel cleanliness and classified by the image classification unit 110 as shown in FIG. 8. In this case, the representative image A is scored '9' points for the small-bowel cleanliness, and a total number of small-bowel images similar to the representative image A is '7' together with the representative image A. Further, the representative image B is scored '8' points for the small-bowel cleanliness, a total number of small-bowel images similar to the representative image B is '3' together with the representative image B. Therefore, the cleanliness diagnosis unit 130 diagnoses the final small-bowel cleanliness by summing up seven similar small-bowel images of the representative image A multiplied by 9 points for the small-bowel cleanliness of the representative image A and three similar small-bowel images of the representative image B multiplied by 8 points for the small-bowel cleanliness of the representative image B, and dividing the sum by a total of ten small-bowel images. This is expressed as follows.

Final small bowel cleanlines =

$$\frac{(7 \text{ images} \times 9 \text{ points}) + \ldots + 3 \text{ images} \times 8 \text{ points}}{10} = \frac{87}{10} = 8.7 \text{ points}$$

Like this, when the cleanliness diagnosis unit 130 finally diagnoses the small-bowel images according to the scores for the small-bowel cleanliness, it is diagnosed that a series of a plurality of small-bowel images received in real time is scored '8.7' for the small-bowel cleanliness.

Embodiments of the disclosure have been disclosed for the illustrative purposes, and it will be appreciated by a person having ordinary skills in the art to which the disclosure pertains that various changes, modifications and additions can be made within the scope of the disclosure, and such changes, modifications and additions fall into the appended claims of the disclosure.

The invention claimed is:

1. A system for diagnosing small-bowel cleanliness, comprising:
   a similarity analysis unit configured to perform analysis for selecting a representative image of similar small-bowel images from among a plurality of small-bowel images;
   an image classification unit configured to classify the plurality of small-bowel images according to scores for small-bowel cleanliness by predicting the small-bowel cleanliness by applying the representative image to a learning result when a series of the plurality of small-bowel images of which the cleanliness is desired to be diagnosed is received in a state that the plurality of small-bowel images has been learned; and
   a cleanliness diagnosis unit configured to calculate final small-bowel cleanliness about the series of the plurality of small-bowel images based on points of the representative image scored for the small-bowel cleanliness and the number of small-bowel images similar to the representative image,
   wherein the learning of the image classification unit comprises scoring the small-bowel cleanliness of the plurality of small-bowel images,
   wherein the image classification unit comprises convolutional neural network (CNN) model,
   wherein the image classification unit is configured to perform the learning after standardizing color references of the plurality of small-bowel images output from a plurality of image sensors,
   wherein the color references employ one or more of RGB (Red, Green, Blue), HSV (Hue Saturation Value), and Lab (Color Coordinates),
   wherein the standardizing color references of the plurality of small-bowel images comprises:
   converting the RGB of the plurality of small-bowel images to a gray scale;
   selecting S component from the HSV of the plurality of small-bowel images; and
   selecting b component from the Lab of the plurality of small-bowel images, and
   wherein the CNN model uses Avg pooling when the HSV is S-scale and the Lab is b-scale, and Max pooling when the RGB is gray.

2. The system of claim 1, wherein the similarity analysis unit is configured to select the representative image by measuring similarity based on comparison in a color histogram between two small-bowel images through a Bhattacharyya distance algorithm and selecting the representative image from among the plurality of small-bowel images selected based on a given similarity reference.

3. The system of claim 2, wherein the given similarity reference converges into '0' as similarity between two small-bowel images decreases, and converges into '1' as the similarity increases.

4. The system of claim 1, wherein the image classification unit is configured to learn color and texture characteristics of the plurality of small-bowel images based on the CNN model, and predict small-bowel cleanliness by applying the small-bowel images to the learning result based on landmark information.

5. The system of claim 1, wherein the plurality of small-bowel images are scored on a scale of '1' to '10' for small-bowel cleanliness.

6. The system of claim 1, wherein the final small-bowel cleanliness is obtained by multiplying the number of similar images corresponding to 1 to $n^{th}$ representative images by points of scored cleanliness, summing up the multiplication results, and dividing the sum by a total number of the plurality of small-bowel images.

7. The system of claim 1, wherein the image classification unit is configured to learn a small-bowel region based on color and texture in the plurality of small-bowel images, and classifies the plurality of small-bowel images according to the small-bowel region based on landmark information set in the small-bowel region.

* * * * *